United States Patent [19]

June et al.

[11] Patent Number: 6,153,790
[45] Date of Patent: Nov. 28, 2000

[54] METHOD TO PRODUCE AROMATIC DICARBOXYLIC ACIDS USING COBALT AND ZIRCONIUM CATALYSTS

[75] Inventors: Raymond Lawrence June, Houston; Michael Wayne Potter, Sugar Land; Edward James Simpson, Houston; Charles Lee Edwards, Houston, all of Tex.

[73] Assignee: Shell Oil Company, Houston, Tex.

[21] Appl. No.: 09/201,963

[22] Filed: Dec. 1, 1998

[51] Int. Cl.$^7$ .................................................. C07C 51/255
[52] U.S. Cl. ............................................................ 562/414
[58] Field of Search ............................................. 532/414

[56] References Cited

U.S. PATENT DOCUMENTS

| | | | |
|---|---|---|---|
| 2,833,816 | 5/1958 | Saffer et al. | 260/524 |
| 3,299,125 | 1/1967 | Ichikawa | 260/524 |
| 3,364,256 | 1/1968 | Ichikawa | 260/525 |
| 3,584,039 | 6/1971 | Meyer | 260/525 |
| 3,660,476 | 5/1972 | Ichikawa et al. | 260/524 R |
| 3,700,731 | 10/1972 | Sullivan | 260/524 R |
| 3,766,258 | 10/1973 | Engelbrech | 260/515 P |
| 3,952,052 | 4/1976 | Sherk | 260/525 |
| 5,523,474 | 6/1996 | Kingsley et al. | |
| 5,686,638 | 11/1997 | Kos et al. | 554/134 |
| 5,693,856 | 12/1997 | Ramachandran et al. | 562/414 |
| 5,696,285 | 12/1997 | Roby | 562/416 |

FOREIGN PATENT DOCUMENTS 1 146 588  5/1983  Canada .

OTHER PUBLICATIONS

"Oxide aromatics over doped cobalt," *Chemtech*, Jun. 1978, 366–371.

Arthur W. Chester et al., "Zirconium Cocatalysis of the Cobalt–Catalyzed Autoxidation of Alkylaromatic Hydrocarbons," *Journal of Catalysis* 46, 308–319 (1977).

National Fire Protection Association 53 Guide on Fire Hazards in Oxygen–Enriched Atmospheres 1994 Edition.

*Primary Examiner*—James O. Wilson
*Assistant Examiner*—Robert W. Deemie
*Attorney, Agent, or Firm*—Del S. Christensen

[57] ABSTRACT

A process to produce terephthalic acid is provided, the process including the steps of: providing a feed stream comprising a dialkyl substituted aromatic and in an organic acid solvent: contacting the feed stream with an oxidant, the oxidant containing at least 50% by volume oxygen and at an oxygen partial pressure of at least 1 psia, at a temperature between about 80° C. and about 130° C., in the presence of a catalyst system comprising zirconium and cobalt, wherein the contacting is done in a stirred tank reactor; removing from the stirred tank reactor a vapor stream comprising the organic acid, water vapor and unreacted oxidant; condensing at least a portion of the organic acid and water from the vapor stream; separating at least a portion of the water from the organic acid back to the stirred tank reactor; returning at least a portion of the condensed organic acid back to the stirred tank reactor; continuously recovering from the stirred tank reactor a product comprising a diacid substituted aromatic; isolating solid crystals of diacid substituted aromatic from the reactor product; and recovering from the solid crystals a diacid substituted aromatic having a purity of preferably at least 97% by weight.

27 Claims, 2 Drawing Sheets

METHOD TO PRODUCE AROMATIC DICARBOXYLIC ACIDS USING COBALT AND ZIRCONIUM CATALYSTS

FIELD OF THE INVENTION

The invention relates to a method to produce aromatic dicarboxylic acids.

BACKGROUND TO THE INVENTION

U.S. Pat. No. 3,299,125 suggests a catalyst system for production of aromatic diacids which utilizes combination of two metals, one being cobalt, and a second being from a group which includes zirconium. This catalyst system is shown to be effective for oxidation of para-xylene to terephthalic acid at temperatures in the preferred range of 80° C. to 130° C. This temperature range is considerably lower than that necessary using other catalyst systems. The oxidation is performed in a solvent such as acetic acid and water, and oxygen or air is bubbled through the reaction medium. At 120° C., reaction times of 8 hours are necessary to achieve conversions of para-xylene to terephthalic acid of sixty to eighty percent. With the combination of cobalt and zirconium as the catalyst, the highest yield of terephthalic acid shown was 88%. This patent describes the advantages of the catalyst system as being the ability to eliminate halide promoters from the catalyst system, thus significantly reducing metallurgy requirements in the reactor system.

U.S. Pat. No. 3,700,731 suggests a cobalt-catalyzed oxidation of para-xylene wherein the reaction is performed in a continuous stirred tank reactor with hold-up times on the order of 240 minutes, with a constant withdraw of product and recycle of unreacted feed and partially oxidized intermediates. The pressure of the reaction system is such that all of the reactants are kept in the liquid phase, and air or air enriched with oxygen up to 50% is preferred as the oxidant. The product removed from the reactor is highly impure, with terephthalic acid crystal purities of about 85%, and a large quantity of partially oxidized intermediates dissolved in the liquid phase. Terephthalic acid is removed from the reactor product by filtering crystals from a cooled reactor product, and then recycling the liquid back to the reactor. The filtered crystals are "digested" by contacting with a solvent such as acetic acid at a temperature of about 200° C. to 300° C. for about ten minutes or longer, and then filtration of the digested crystals at about 100° C. and washing with hot water or acetic acid. These process operations result in a rather large recycle stream of partially oxidized intermediates to the oxidation reactor. A final terephthalic acid product is said to be 98 to 99% pure with a yield based on the starting para-xylene of 95% (molar). While the oxidation of para-xylene to terephthalic acid is highly exothermic, this patent is silent about how the oxidation reaction is cooled. Although adequate cooling of the stirred tank reactor can be achieved in a laboratory environment, it is a significant factor in design of the commercial reaction system because the produced terephthalic acid is sparingly soluble in the reaction solution. Crystals can therefore precipitate on heat exchange surfaces if temperatures of the heat exchange surfaces are significantly less than the temperature of the reaction mixture, resulting in ineffective heat removal.

The vast majority of commercially available terephthalic acid is produced by improved versions of U.S. Pat. No. 2,833,816, which suggests a catalyst combination of cobalt and manganese salts and a halide promoter, for example bromine. In this system, para-xylene is contacted with air in an acetic acid medium at temperatures in the range of 170° C. to 210° C., and so-called "crude" terephthalic acid is produced. Over time, these systems have been improved to the point where typical crude terephthalic acid purities of 98–99.5% are produced in yields of roughly 95–96% molar based on para-xylene feed with oxidizer contact times of 45–90 minutes. However, this system suffers from significant acetic acid decomposition in the range of 5–10 lb/100 lb of terephthalic acid produced. In addition, the acetic acid and halide promoters are highly corrosive, necessitating the use of higher metallurgy as the material of contact, namely titanium. The contributions of acetic acid losses and titanium metallurgy significantly increase manufacturing costs.

U.S. Pat. No. 5,523,474 suggests a catalyzed system with bromine promotion for para-xylene oxidation in an acetic acid medium. The reactor design is a so-called liquid oxygen reactor (LOR) which utilizes oxygen-enriched air in purities of 50–100% oxygen by volume. The benefits claimed include lower acetic acid decomposition and reduction in premature reactor shutdowns. While the patent describes the bromine-promoted system which requires titanium metallurgy, it fails to address the significant flammability concern associated with the incompatibility of oxygen-enriched air and titanium as is well known in industry and indicated in National Fire Protection Association 53 Guide on Fire Hazards in Oxygen-Enriched Atmospheres 1994 Edition.

For each of the oxidation techniques discussed above, after isolation the resulting terephthalic acid solids are generally referred to as "crude" terephthalic acid. The crude terephthalic acid can be up to 99.5% purity, with the primary impurities being 4-carboxybenzaldehyde (hereafter referred to as 4-CBA), para-toluic acid (hereafter referred to as pTA), and color containing species. Such a product is not of sufficient purity to be used directly for polyester fiber or bottle resins without additional purification, most typically by hydrogenation and re-crystallization. An example of such a purification technique is U.S. Pat. No. 3,584,039.

There is also significant commercial interest in production of isophthalic acid by oxidation of meta-xylene. Isophthalic acid is typically produced by processes similar to those used for terephthalic acid.

It would be desirable to have a process to produce these dicarboxylic aromatics wherein high yields and conversions are obtainable, wherein titanium equipment is not required, and wherein solvent decomposition is decreased. It is therefore an object of the present invention to provide an improved process for production of aromatic diacids having high yields and conversions, high crystal purities and reduced solvent decomposition losses.

SUMMARY OF THE INVENTION

These and other objects are achieved by a process to produce diacid substituted aromatics with a purity of at least 97%, the process comprising the steps of: providing a feed stream comprising a dialkyl substituted aromatic and in an organic acid solvent: contacting the feed stream with an oxidant, the oxidant containing at least 50% by volume oxygen and at an oxygen partial pressure of at least 1 psia, at a temperature between about 80° C. and about 130° C., in the presence of a catalyst system comprising zirconium and cobalt, wherein the contacting is done in a stirred tank reactor; removing from the stirred tank reactor a vapor stream comprising the organic acid, water vapor and unreacted oxidant; condensing at least a portion of the organic acid and water from the vapor stream; separating at least a portion of the water from the organic acid back to the stirred tank reactor; returning at least a portion of the condensed organic acid back to the stirred tank reactor; continuously recovering from the stirred tank reactor a product comprising a diacid substituted aromatic; isolating solid crystals of diacid substituted aromatic from the reactor product; and recovering from the solid crystals a diacid substituted aromatic having a purity of preferably at least 97% by weight. Use of oxygen or significantly enriched air in the practice of the present invention along with reflux cooling by removing solvent vapors, and returning a portion of the condensed solvent, provides an effective partial pressure of oxygen for the oxidation reaction and avoids the presence of heat exchange surfaces in the reactor. Removal of water from the reflux provides an effective way to purge water created by the oxidation reaction.

The process also preferably includes a step wherein the isolated solid crystals of diacid substituted aromatics are contacted with additional solvent at a temperature of between about 150° C. and 250° C. for about 10 30 to 60 minutes. The additional solvent may be water or organic acid such as acetic acid, or mixtures thereof. The additional solvent preferably does not contain significant concentrations of oxidation byproducts and/or oxidation catalysts. This additional soaking step could be repeated to further improve purity. When isophthalic acid is produced by the present invention, a second soaking step is preferred because of the resultant product can be pure enough for polymerization without further processing. When terephthalic acid is produced, the second soaking step is not normally preferred because the resulting product will likely require further processing before polymerization (for example, hydrotreating and recrystalization) even with a second soak step. The final soak step could utilize water rather than organic acid so that the final product would contain less of the organic acid. Additionally, if water is used as the solvent for any soak step, air or oxygen could be added to achieve some additional oxidation. Addition of oxidant during a soak step with organic acid as the solvent (or a significant amount of organic acid present) would not be preferred because oxidation of the organic acid could occur.

In a preferred embodiment, the dialkyl-substituted aromatic is para-xylene, which is oxidized to terephthalic acid and/or meta-xylene, which is oxidized to isophthalic acid.

DESCRIPTION OF A PREFERRED EMBODIMENT

The method of the present invention utilizes an oxidation catalyst which has been found to be particularly effective for oxidation of aromatic alkyl groups to carboxyl groups. The catalyst system is a combination of a cobalt and a zirconium species. The cobalt and the zirconium may be in any form that is soluble in the reaction medium. Examples of such soluble forms include: organic acid salts, basic salts, complex compounds, and alcoholates. The amount of cobalt is generally between about 0.01 and about 1 molar in the reaction solution. The ratio of cobalt to zirconium is preferably not greater than about 3:1 and more preferably greater than about 7:1 molar. The catalyst can be added to the reaction mixture with the reactants or separately. The catalysts are preferably recycled from the solution of reactants by recycling the solution after the desired products have been removed by, for example, precipitation and/or filtration.

Other metals and promoters may be present in the catalyst system of the present invention, but the two metal system has been found to be effective. For example, halide promoters may be included, but it has been found that increases in activity are offset by greater metallurgy requirements. The absence of halide promoters is therefore preferred.

Figure 1:
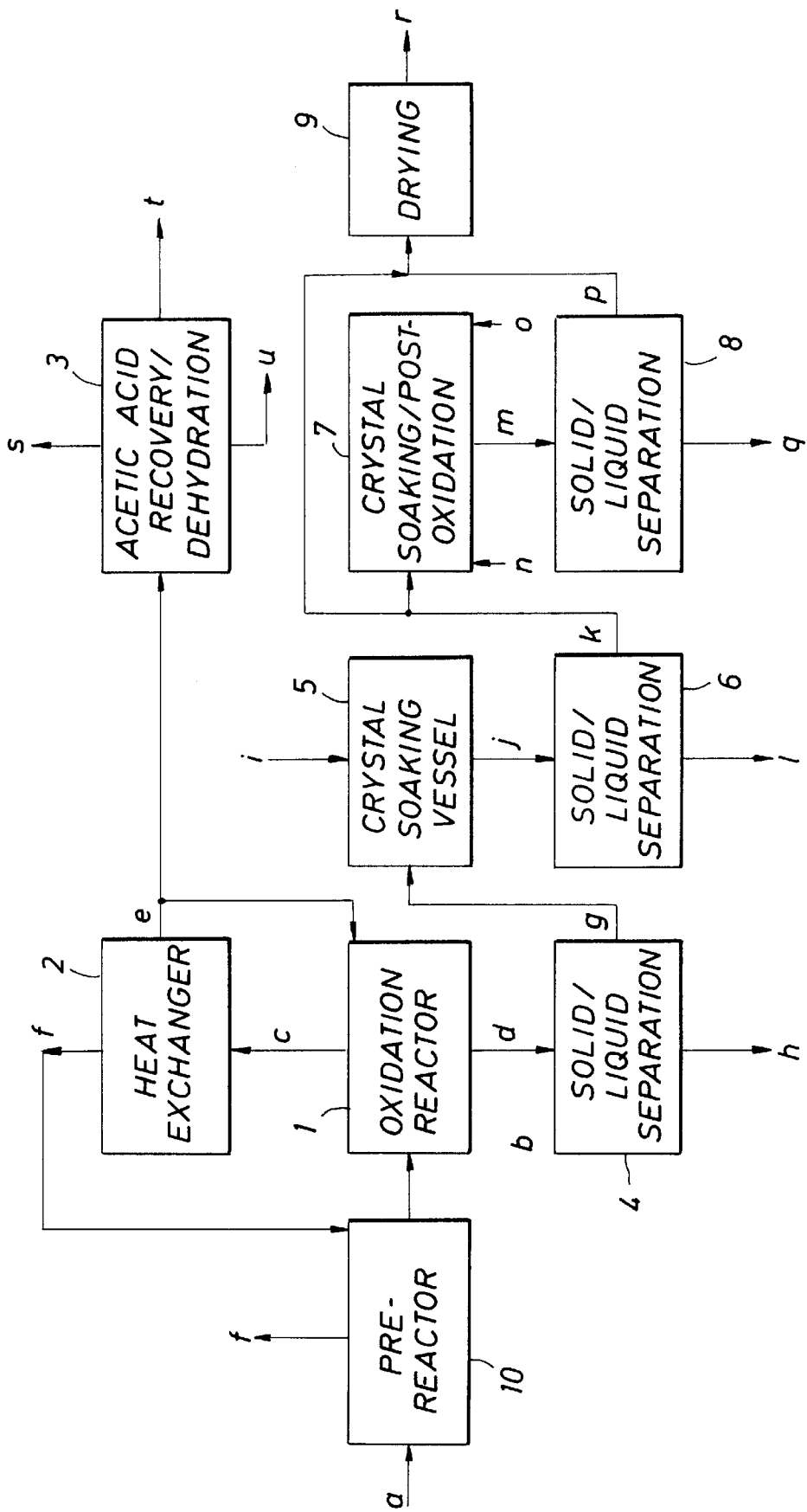
FIG. 1 is a process flow diagram of a process for manufacturing aromatic carboxylic acids utilizing the present invention.

Referring now to FIG. 1, the species oxidized by the invention of the present invention is a dialkyl substituted aromatic a provided to reactor 1. The dialkyl-substituted aromatic may be combined with the catalyst materials, or the catalyst materials could be added to the reactor separately. Para-xylene and meta-xylene are especially preferred dialkyl substituted aromatics because the resultant products are commercially valuable. Mixtures of para-xylene and meta-xylene are also commercially useful. Ethylbenzene and toluene can also be contained in unpurified xylene streams. Various oxidation intermediates of the above substituted aromatics could also be used as starting feed materials, for example para-toluic acid, para-tolualdehyde, or 4-carboxybenzaldehyde in the case of terephthalic acid being the desired product. The feeds of the present invention are provided in a solution with an organic acid solvent in stream a. Preferable organic acids include organic acids having from two to four carbons with one carboxyl group. The most preferred solvent is acetic acid due to its vapor pressure at preferred reactor temperatures, and its solvent capabilities. These organic acids are solvents for reasonable concentrations of the feed components, the catalyst system components, and the intermediate products. The feed is preferably provided in a solution of between about 5 and about 25 weight percent.

The dialkyl substituted aromatic is oxidized by a vapor or liquid b initially containing at least 50% by volume oxygen which is added to reactor 1 in vapor or liquid b, at an oxygen partial pressure of between about 1 psia and about 20 psia and preferably between about 3 and about 15 psia. More than 50% by volume oxygen is required so that the total pressure of the reaction system can be low enough to allow reflux cooling of the reaction system at temperatures of between about 80° C. and about 130° C., and more preferably of between about 110° C. and about 120° C. The reflux cooling is a result of vaporization of liquid phase components due to boiling and gas stripping, creating vent stream c. Reflux cooling results in a uniform reaction temperature, the only differences in temperature throughout the reactor being attributable to static head and some local differences in compositions of the solution. Further, reflux cooling eliminates cooling surfaces within the reaction vessel. It is important to eliminate cooling surfaces within the reaction vessel because the oxidized products of the present invention would tend to precipitate on the cooling surfaces and foul the surfaces. Further, the uniform temperatures of the present invention are desirable because uniform reaction temperatures reduce undesirable side reactions. The vapor stream b may be sparged into a liquid level in a reactor, and the noncondensable vapors in stream c from the reactor are either recycled or vented, but the condensable solvent and water vapors in the vent stream c are condensed in heat exchanger 2 for recovery. A portion of the condensed liquids e may be returned to the reactor, while a portion may also be directed to a solvent recovery system 3 for removal of water from the solvent/water mixture.

The reaction of the present invention takes place in a stirred tank reactor 1 with an essentially continuous addition of reactants and withdrawal of products.

Product purities increase considerably when an essentially continuous stirred tank reactor is utilized as opposed to a batch or plug flow reactor. Useful reactors may have baffles to improve contact of the sparged vapors with the liquids in the reactor, thus not being a perfect stirred tank reactor. But a significant portion of the volume is preferably subjected to significant back mixing and agitation, for example, with an impeller or jets. Because halide promoters are not necessary and the reaction is performed at relatively low temperatures, the corrosivity of the reaction medium is not particularly high. This allows use of stainless steel metallurgy as the primary material of contact. Use of stainless steel has the advantage over titanium from the standpoint of both cost and safety in high oxygen concentration environments. For economic reasons, the stainless steel can be constructed as a inner cladding as the material of contact with a less expensive outer layer of carbon steel. The reactor design must also effectively provide for nearly complete oxygen consumption below the liquid/gas interface. Nitrogen can be injected in the vicinity of the liquid/gas interface in a quantity rendering the vapor phase gas mixture non-flammable. If desired, after dilution with nitrogen the unconsumed oxygen f can be contacted with the feed streams in optional pre-reactor 10 to provide nearly or fully complete oxygen utilization.

The oxidation of the alkyl aromatic with the oxygen stream results in production of reaction water. This reaction water may be accumulated in the system to a concentration less than about 15 weight percent and preferably between about 3 and about 10 weight percent. It has been found that the catalyst system of the present invention is surprisingly sensitive to the presence of water in greater amounts. Some water may also be included in the feed stream to supplement the reaction water present to control solubility of the reactants, or to control the temperature and cooling of the reactor.

The unvaporized portion of the reactor contents containing both liquid and solid are essentially continuously withdrawn as stream d and sent to a suitable solid/liquid separator 4, which produces solids g containing aromatic diacid crystals with some solvent and mother liquor h. The solid/liquid separation device effectively isolates the solid crystals from the liquid, and can in some cases also be provided with means to wash the crystals with a suitable solvent. The temperature at which the solid/liquid separation is performed is preferably between about 30° C. and 130° C. and more preferably between about 50° C. and 80° C. Examples of acceptable wash liquids include lower organic acids and aqueous solutions thereof, and water. Acetic acid is most preferred, with an aqueous content less than about 15% water. Examples of suitable solid/liquid separation devices include centrifuges and pressure filters. At elevated temperatures and pressures when crystal rinsing is the main objective, the Merco Disc-Nozzle centrifuge (Dorr-Oliver, Milford, Conn.) is a particularly preferred low cost choice as the solid/liquid separation device. After the solid crystals of the aromatic diacid have been sufficiently washed, they can be furthered exposed to a crystal soaking operation in continuously stirred tank 5. If desired, additional solvent i can be added. Additional solvent may be water, an organic acid, or a mixture thereof, but preferably does not contain a significant amount of partially oxidized alkyl aromatics. Most preferred is a acetic acid with less than about 15% (w/w) water. The temperature at which the crystal soaking operation is performed is preferably between about 150° C. and 250° C. and more preferably between about 180° C. and 220° C. The contact time for the crystal soaking step is preferably between about 5 and about 120 minutes and more preferably between about 10 and about 60 minutes. The ratio of aromatic feed to solvent is preferably between about 1:1 (w/w) and 1:10 and more preferably between about 1:2 and 1:5. The resulting crystals are discharged as a slurry j. If the crystal soaking operation is performed in the presence of acetic acid, nitrogen is preferably used to provide an inert environment, thus preventing oxidative degradation of the acetic acid, discoloration of the aromatic diacid crystals, and corrosion of the vessels.

When the aromatic feed is meta-xylene, the crystal soaking operation can be performed at more mild conditions, also in a continuously stirred tank. In this embodiment of the present invention the temperature at which the crystal soaking operation may be performed is preferably between about 120° C. and 220° C. and more preferably between about 140° C. and 200° C.

After the initial crystal soaking is performed on the aromatic diacid crystals, an additional solid/liquid separation operation can be performed in separator 6, producing solvent 1 and crystal stream k. Any rinsing liquid used in solid/liquid separation devise 6 is preferably water or acetic acid. The temperature at which the solid/liquid separation may be performed is preferably between about 50° C. and 200° C. and more preferably between about 80° C. and 180° C. These temperature ranges have the particular advantage of preventing the re-deposition of oxidation intermediates onto the desired crystal product.

The crystal stream k can be furthered processed in a continuously stirred crystal-soaking vessel 7 and/or dryer 9, or used without further processing if desirable.

When utilizing a crystal-soaking vessel 7, the temperature is preferably between about 120° C. and 220° C. and more preferably between about 150° C. and 200° C. The contact time for the crystal soaking step is preferably between about 5 and about 120 minutes and more preferably between about 10 and about 60 minutes. The ratio of aromatic feed to water is preferably between about 1:1 (w/w) and 1:10 and more preferably between about 1:2 and 1:5 which can be adjusted by addition of solvent o. Solvent o can be water, an organic acid, or mixtures thereof. Water and acetic acid with 0–10% water are the most preferred choices. Upon completion of the crystal soaking operation, the wet aromatic diacid crystals m are isolated by a solid/liquid separation and rinse in separator 8, producing a wet aromatic diacid p, recovered solvent q, and dried in dryer 9 to produce an aromatic diacid crystals r, which, in the practice of the present invention, will have a purity of greater than about 97% by weight. The temperature at which the solid/liquid separation may be performed is preferably between about 50° C. and 180° C. and more preferably between about 80° C. and 130° C.

One embodiment of the present invention includes utilizing a continuously stirred vessel as the crystal soaking vessel 7, and injecting air n to contact the aromatic diacid crystals to further oxidize intermediate impurities. When air is injected, the solvent is preferably water to so that solvent oxidation does not occur.

The crystal soaking step is found to be particularly effective production of isophthalic acid due to a relatively high solubility of each of the meta isomers in water. This high solubility lowers the required operation temperature, preventing formation of color bodies. The lower operating temperatures allow consideration of the addition of air or oxygen to vessels 5 and 7 to promote further reaction of oxidation intermediates while avoiding significant solvent and product degradation. No catalyst addition is required in these steps and the resulting isophthalic acid product can be utilized directly in polyester applications without further purification.

It is most preferred that the last solid/liquid separator used prior to sending crystals to dryer 9 have means for formation of a cake. The separator preferably has a capability to reduce the moisture content of the crystals to less than 25% (w/w) and most preferably to below about 10%. Examples of such solid/liquid separators include pressure filters and centrifuges. If water is not chosen as the solvent for the final crystal soaking operation, it is also preferred that any rinse liquid used in the last solid/liquid separator be water, so as to limit the residual content of solvent in the product.

Portions of organic acid streams e, h, l, and q can be either returned to reactor 1 or sent to solvent recovery and dehydration system 3. The solvent dehydration system 3 produces stream s (mainly water), stream t (mainly purified acetic acid), and stream u (mainly heavy ends residue and catalysts for recovery).

EXAMPLE 1

A 316 stainless steel reactor was operated with continuous feed addition and product removal at temperatures between about 110° C. and 130° C. with residence times of one to two hours, and a feed stream of 5 to 20 weight percent para-xylene in acetic acid with a catalyst system of zirconium acetate $[ZrO^*(AcO)_2]$ and cobalt acetate with cobalt concentrations of 0.05 to 0.15 molar, and a cobalt to zirconium molar ratio of 7:1. The reactor was cooled with cooling coils and air was sparged into the reactor through a subsurface diptube. Acetic acid solution containing the catalyst and para-xylene feed were delivered via a positive displacement metering pump and product was continuously removed via pulsed flow through a control valve in the bottom of the reactor. Gas feed rates were monitored with mass flow controllers. The pressure was maintained at about 240 psia. Water was added to the feed in concentrations of up to 5% by weight in some runs. The reactor was provided with an air driven gas-dispersing impeller.

While the temperature was adequately controlled via cooling coils, upon inspection of the reactor internals, it was observed that dramatic fouling occurred on the cooling coils. It is inferred that such fouling would render a commercial system inoperable, necessitating use of evaporative cooling for extended operation.

The product from the continuous reactor was cooled to about 50° C., and precipitate was collected on a filter. The precipitate was prepared for analysis by combining the precipitate with 95:5 (w/w) acetic acid/water at 110° C. for a time period of 30 minutes. The resultant crystals were analyzed and purities of terephthalic acid of up to 97% percent by weight were produced, with the most significant impurities being para-toluic acid and 4-CBA. Samples of the vent gas were regularly analyzed by gas chromatography for oxygen ($O_2$), carbon monoxide (CO), and carbon dioxide ($CO_2$). Liquid and solid products were analyzed with HPLC using a 25 cm×4.6 mm C18 column with a water/acetonitrile/methanol gradient elution program.

Results from the Examples are reported in Table 1. Methyl group conversion is defined as:

$$\frac{\text{mol methyl group consumed}}{\text{mol methyl group charged}}$$

and was computed from vent gas analysis as follows:

$$\frac{(O2 \text{ uptake from air} - O2 \text{ used in } CO2) \text{LPM}}{\frac{22.4 L/\text{mol} * 1.5 \text{ mol } O2/\text{methyl group}}{\frac{g \text{ xylene/min in feed}}{106.1 g/\text{mol} * 2 \text{ methyl groups}/\text{xylene}}}}$$

where the GC based vent gas analysis was used to determine the oxygen, carbon monoxide, and carbon dioxide concentrations in the vent gas. The burn rate is defined as:

$$\frac{\frac{(CO + CO_2) \text{ mol in vent}}{8 \text{ mol } COx/\text{mol xylene}}}{\text{mol } PX \text{ converted in feed}}$$

where the vent gas analysis was again used to compute the carbon oxide production rate and the xylene conversion was computed from the conversion described above. All combustion products were allocated to the xylene in the feed. An alternate assumption of acetic acid burning would result in a number differing only by the carbon content of the molecules. Overall vent gas concentrations of carbon oxides ($CO+CO_2$) were about 0.8%.

In a specific experiment, the reactor was operated at 120° C. and 240 psia with a catalyst concentration of 0.137 molar cobalt and a 7:1 ratio of Co/Zr. Para-xylene in the feed was 9 percent by weight. The liquid phase holdup time (residence time) in the reactor was 120 minutes. Results for this experiment are shown in Table 1. For this example, the methyl group conversion was 96.6% and about 1.7% of the para-xylene molecules were lost in the vent gas. This corresponds to a reaction selectivity of approximately 98.3% based on para-xylene, given the assumption of negligible acetic acid decomposition. If small amounts of acetic acid are decomposed in the reaction, the selectivity should actually be a higher value. The rinsed crystals from this example were 96.6% terephthalic acid purity and contained 2.2% para-toluic acid and 1.1% 4-CBA. The crystals were a bright white, fine powder.

EXAMPLE 2

Comparative

A batch oxidation was carried out in the apparatus described in Example 1 at 120° C. and 290 psia by charging the autoclave with a mixture of 13% para-xylene in acetic acid. Cobalt acetate was added at a concentration of 0.1 molar to the acetic acid with a cobalt to zirconium ratio of 7:1 (molar). The oxidation was performed by starting a mixed nitrogen/air flow and then backing out the nitrogen as the catalyst became activated. The oxidation reaction was run for about 1.5 hours after which air addition was ceased. While at 120° C., the mother liquor was drained from the vessel through a porous frit on the bottom of the vessel. Then hot acetic acid was used to re-slurry and wash the crystals at 120° C. for about 5 minutes. After drying, the resulting terephthalic acid crystals had a purity of about 84.6% with 5.7% 4-CBA and 9.7% pTA. With the unsteady nature of the experiment, an accurate gas phase analysis could not be obtained.

When compared to EXAMPLE 1, this comparative example shown the significance of using a stirred tank reactor rather than a batch reaction system.

EXAMPLE 3

Comparative

An oxidation reaction was performed in the apparatus used in Example 1. The reaction pressure was lowered to 55 psia and the vessel was operated at 120 C with a 120 minute residence time. The cobalt catalyst concentration in glacial acetic acid was 0.1 molar with a 7:1 Co/Zr ratio. With a vent oxygen concentration of 4% (v/v), an oxygen partial pressure in the dry vent gas of only 2.2 psia is obtained. As shown in Table 1, the conversion was 32.4% and the aromatic burn rate was 4.6%. Under these oxygen starved conditions, the aromatic burn rate was significantly higher and very few solids were present in the reaction product indicating that only a small fraction of the product was converted to terephthalic acid. This example illustrates that operating with oxygen unenriched air at a pressure which would allow evaporative cooling provides an ineffective oxygen partial pressure for the reaction with respect to product purities and reaction rate.

EXAMPLE 4

An oxidation reaction was performed as in Example 1 with a mixture of 95:5 (w/w) para-xylene/meta-xylene at 13% in glacial acetic acid. The catalyst was 0.1 molar cobalt with a Co/Zr ratio of 7:1. Temperature and pressure were again 120° C. and 240 psia with a 108 minutes holdup time. The product of this reaction was crystals of a mixture of terephthalic acid and isophthalic acid, with a diacid purity of 93.3%. The remaining composition of the crystals was comprised largely of 6.7% pTA and 2.0% 4-CBA and low levels of mTA and 3-CBA. As shown in Table 1, the conversion was 95.1% and the aromatic burn rate was 1.2%, indicating a xylene selectivity of 98.8%, assuming negligible acetic acid decomposition. The crystals were a bright white, fine powder.

EXAMPLE 5

An oxidation reaction was performed as in Example 4 with 100% meta-xylene. The unit was operated with a 115 minute holdup time at 120° C. and 240 psia. The catalyst was 0.1 molar cobalt acetate and a molar ratio of cobalt to zirconium of 7:1. As shown in Table 1, a high methyl group conversion was obtained, suggesting that the catalyst system is slightly more active with meta-xylene than para-xylene. The burn rate was 1.5%, indicating a selectivity of 98.5% based on meta-xylene. The product isophthalic acid crystals were 98.8% pure, indicating a significantly higher purity than in the case of terephthalic acid. The crystals were a bright white, fine powder.

EXAMPLE 6

Comparative

A halide promoted oxidation was performed to compare the relative burning losses of the two types of catalyst systems. A Hastalloy C reactor was constructed similarly to the stainless steel unit described in Example 1 and was operated in a semi-batch fashion with an initial charge of acetic acid and catalyst (Co/Mn/Br). To avoid a high initial concentration of reactant, para-xylene was fed continuously to the reactor at a rate of 70 g/hr. The catalyst make up was 0.52 g of manganese acetate tetrahydrate, 0.18 g of cobalt acetate tetrahydrate, and 0.29 g of 48% HBr solution dissolved in 280 g of acetic acid containing 17.5 g of water. The oxidation was run at 205° C. and 420 psia with the catalyst and solvent initially charged to the reactor. After the feed of para-xylene was completed, the temperature was lowered to 185° C. and the oxidation was completed with an additional minutes of post-oxidation to scavenge any remaining partially oxidized species in the mother liquor and to partially age the crystals. Results in Table 1 demonstrate essentially complete conversion of the para-xylene with burning losses of 3.6%. In this case, it is known that the burning losses may be attributed to both para-xylene and acetic acid. In comparison with Examples 1, 4, and 5, the losses are greater than twice the amount of losses of the present invention.

EXAMPLE 7

The manner of oxidations demonstrated in examples 1, 4, and 5 produce crystals which are amenable to further purification by exposure to a higher temperature wash stream for a time sufficient to allow partial dissolution and re-precipitation of the crystals.

A sample of oxidation product produced in a manner similar to Example 1 was combined with acetic acid with a ratio of acetic acid to terephthalic acid of 9:1 and heated to 200° C. in a continuously stirred reactor with a blanket of $N_2$ for a holdup time of 30 minutes. The resulting slurry was cooled to approximately 100° C. and filtered. The starting material had a purity of 91.7% terephthalic acid, with 5.8% pTA and 2.9% 4-CBA. After the crystal soaking step, the crystal purity was 98.4% terephthalic acid, with 0.88% pTA and 0.72% 4-CBA. The crystals were a bright white, fine powder, with no significant apparent color change versus the starting material.

EXAMPLE 8

A sample of oxidation product from Example 5 was combined with acetic acid with a ratio of acetic acid to isophthalic acid of 4:1 and heated to 200° C. in a continuously stirred reactor with a blanket of $N_2$ for a holdup time of 30 minutes. The resulting slurry was cooled to approximately 100° C. and filtered. The starting material had a purity of 98.9% isophthalic acid, with 0.92% mTA and 0.24% 3-CBA. After the crystal soaking step, the crystal purity was 99.97% isophthalic acid, with no detected mTA and 0.03% 3-CBA. The crystals were a bright white, fine powder, with no significant color change versus the starting material.

EXAMPLE 9

A sample of oxidation product from Example 8 was combined with acetic acid with a ratio of acetic acid to isophthalic acid of 4:1 and heated to 200° C. in a continuously stirred reactor with a blanket of $N_2$ for a holdup time of 30 minutes. The resulting slurry was cooled to approximately 100° C. and filtered. The starting material had a purity of 98.97% isophthalic acid, with no detected mTA and 0.03% 3-CBA. After the crystal soaking step, the crystal purity was 99.996% isophthalic acid, with no detected mTA and 0.004% 3-CBA. The crystals were a bright white, fine powder, with no significant color change versus the starting material.

EXAMPLE 10

Figure 2:
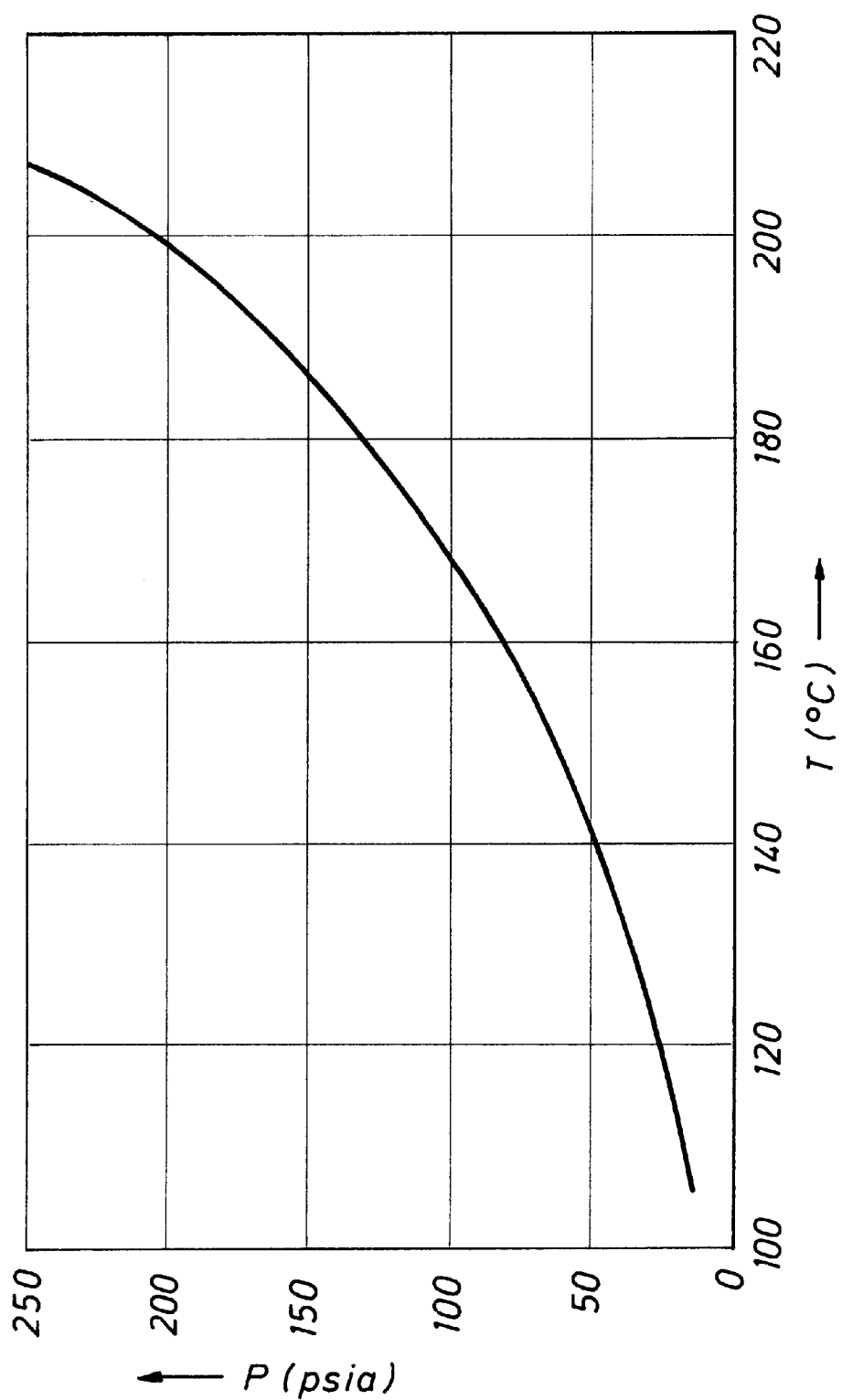
FIG. 2 is a graph showing calculated pressures of operation relating to example 10.

The need to operate the main oxidizer at low pressures so that reflux cooling can be utilized is most easily demonstrated with computer simulation. An Aspen 9.3 simulation using a RSTOIC block operated adiabatically was used to model the main oxidizer. The effluent from the RSTOIC block was then adiabatically flashed to generate a vapor and liquid stream. To avoid the complication of coupling the condensed overhead product with an acetic acid dehydration column, the reflux, containing over 20% water, was simply returned to the reactor. The liquid portion from the flasher was removed as product. The vapor portion leaving the flasher was cooled and the liquid condensate was returned to the reactor. The oxidizer model was operated at 99.9% para-xylene conversion with a 3% burning loss to carbon dioxide. Air was fed so that the vent gas contained 3.5% oxygen on a dry gas basis and the feed contained 15% para-xylene and 5% water in acetic acid. Results from the simulations conducted at a series of pressures are presented in FIG. 2. The results demonstrate that to keep an operable oxygen partial pressure (>1 psia oxygen partial pressure and preferably greater than >10 psia) at temperatures lower than 130° C., an oxygen rich feed is required to allow cooling of the reactor by boiling. The higher pressures required with air to provide the necessary oxygen partial pressure would prevent boiling of the reactor contents.

TABLE 1

Results from Examples

| Example | Targeted Product[1] | Conversion | Burn Rate | % diacid | % toluic acid |
|---|---|---|---|---|---|
| 1 | TPA | 96.6 | 1.7 | 96.6 | 2.2 |
| 2 | TPA | NA | NA | 84.6 | 9.7 |
| 3 | TPA | 32.4 | 4.6 | NA | NA |
| 4 | TPA/IPA mixture | 95.1 | 1.2 | 93.3 | 6.7 |
| 5 | IPA | 99.2 | 1.5 | 98.9 | 0.63 |
| 6 | TPA | 101.5 | 3.6 | 99.5 | 0.45 |
| 7 | TPA | — | — | 98.4 | 0.88 |
| 8 | IPA | — | — | 99.97 | nd |
| 9 | IPA | — | — | 99.996 | nd |

[1]TPA stands for terephthalic acid, IPA stands for isophthalic acid, and nd stands for none detected. For TPA, impurities listed are 4-CBA and pTA. For IPA, impurities listed are 3-CBA and mTA.

We claim:

1. A method to produce an acid substituted aromatic from an alkyl substituted aromatic, the method comprising the steps of:

providing a feed stream comprising a dialkyl substituted aromatic and in an organic acid solvent:

contacting the feed stream with an oxidant, the oxidant containing at least 50% by volume oxygen and at an oxygen partial pressure of at least 1 psia, at a temperature between about 80° C. and about 130° C., in the presence of catalyst system comprising zirconium and cobalt, wherein the contacting is done in a stirred tank reactor;

removing from the stirred tank reactor a vapor stream comprising the organic acid, water vapor and unreacted oxidant;

condensing at least a portion of the organic acid and water from the vapor stream;

separating at least a portion of the water from the organic acid back to the stirred tank reactor;

returning at least a portion of the condensed organic acid back to the stirred tank reactor;

continuously recovering from the stirred tank reactor a product comprising a diacid substituted aromatic;

isolating solid crystals of diacid substituted aromatic from the reactor product;

recovering from the solid crystals a diacid substituted aromatic having a purity of at least 97% by weight wherein the step of recovering from the solid crystals of diacid substituted aromatics a diacid substituted aromatic having a purity of at least 97% comprises a step of contacting the isolated crystals of diacid substituted aromatic with a first solvent for a time period of between about 5 and about 120 minutes and separating crystals of diacid substituted aromatics from the first solvent and then contacting the separated crystals of diacid substituted aromatic with a second solvent for a time period of between about 5 and about 120 minutes.

2. The method of claim 1 wherein the mole ratio of cobalt to zirconium is greater than about 3.

3. The method of claim 1 wherein the temperature of the stirred tank reactor is between 110° C. and 120° C.

4. The method of claim 1 wherein the alkyl substituted aromatic is a xylene.

5. The method of claim 4 wherein the xylene is para-xylene.

6. The method of claim 1 wherein the organic acid is acetic acid.

7. The method of claim 6 wherein the concentration of the alkyl substituted aromatic in the acetic acid is between about 5 and about 25 weight percent based on the total feed.

8. The method of claim 1 wherein the feed stream further comprises between 0 and 5 percent by weight water.

9. The method of claim 1 wherein the zirconium is in the form selected from the group consisting of organic acid salts, basic salts, complex compounds, and alcoholate.

10. The method of claim 1 wherein the cobalt is in the form selected from the group consisting of organic acid salts, basic salts, complex compounds, and alcoholate.

11. The method of claim 1 wherein the feed stream further comprises a recycle of partially oxidized aromatics.

12. The method of claim 3 wherein the dialkyl substituted aromatic is para-xylene and the organic acid is acetic acid.

13. The method of claim 1 wherein the first solvent and the second solvent comprise acetic acid.

14. The method of claim 1 wherein the first solvent and the second solvent comprise water.

15. The method of claim 1 wherein the first solvent is acetic acid and the second solvent is water.

16. A method to produce an acid substituted aromatic from an alkyl substituted aromatic, the method comprising the steps of:

providing a feed stream comprising a dialkyl substituted aromatic and in an organic acid solvent:

contacting the feed stream with an oxidant, the oxidant containing at least 50% by volume oxygen and at an oxygen partial pressure of at least 1 psia, at a temperature between about 80° C. and about 130° C., in the presence of a catalyst system comprising zirconium and cobalt, wherein the contacting is done in a stirred tank reactor;

removing from the stirred tank reactor a vapor stream comprising the organic acid, water vapor and unreacted oxidant;

condensing at least a portion of the organic acid and water from the vapor stream;

separating at least a portion of the water from the organic acid back to the stirred tank reactor;

returning at least a portion of the condensed organic acid back to the stirred tank reactor;

continuously recovering from the stirred tank reactor a product comprising a diacid substituted aromatic;

isolating solid crystals of diacid substituted aromatic from the reactor product: and recovering from the solid crystals a diacid substituted aromatic having a purity of at least 97% by weight wherein the temperature of the stirred tank reactor is between 110° C. and 120° C., the dialkyl substituted aromatic is para-xylene and the organic acid is acetic acid and the method further comprises a step of contacting the precipitate of terephthalic acid with an aqueous wash water stream at a temperature of between about 80° C. and about 120° C.

17. The method of claim 16 wherein the precipitated terephthalic acid is contacted with the wash water for a period of between about 10 and about 60 minutes.

18. A method to produce an acid substituted aromatic from an alkyl substituted aromatic, the method comprising the steps of:

provide a feed stream comprising a dialkyl substituted aromatic and in an organic acid solvent:

contacting the feed stream with an oxidant, the oxidant containing at least 50% by volume oxygen and at an oxygen partial pressure of at least 1 psia, at a temperature between about 80° C. and about 130° C., in the presence of a catalyst system comprising zirconium and cobalt, wherein the contacting is done in a stirred tank reactor;

removing from the stirred tank reactor a vapor stream comprising the organic acid, water vapor and unreacted oxidant;

condensing at least a portion of the organic acid and water from the vapor stream;

separating at least a portion of the water from the organic acid back to the stirred tank reactor;

returning at least a portion of the condensed organic acid back to the stirred tank reactor;

continuously recovering from the stirred tank reactor a product comprising a diacid substituted aromatic;

isolating solid crystals of diacid substituted aromatic from the reactor product; and recovering from the solid crystals a diacid substituted aromatic having a purity of at least 97% by weight wherein the temperature of the stirred tank reactor is between 110° C. and 120° C., the dialkyl substituted aromatic is para-xylene and the organic acid is acetic acid and the method further comprises a step of contacting the precipitate of terephthalic acid with a wash stream comprising an organic acid at a temperature of between about 80° C. and about 120° C.

19. A method to produce an acid substituted aromatic from an alkyl substituted aromatic, the method comprising the steps of:

providing a feed stream comprising a dialkyl substituted aromatic and in an organic acid solvent:

contacting the feed stream with an oxidant, the oxidant containing at least 50% by volume oxygen and at an oxygen partial pressure of at least 1 psia, at a temperature between about 80° C. and about 130° C., in the presence of a catalyst system comprising zirconium and cobalt, wherein the contacting is done in a stirred tank reactor;

removing from the stirred tank reactor a vapor stream comprising the organic acid, water vapor and unreacted oxidant;

condensing at least a portion of the organic acid and water from the vapor stream;

separating at least a portion of the water from the organic acid back to the stirred tank reactor;

returning at least a portion of the condensed organic acid back to the stirred tank reactor;

continuously recovering from the stirred tank reactor a product comprising a diacid substituted aromatic;

isolating solid crystals of diacid substituted aromatic from the reactor product; and recovering from the solid crystals a diacid substituted aromatic having a purity of at least 97% by weight wherein the dialkyl substituted aromatic is meta-xylene and the organic acid is acetic acid.

20. The method of claim 19 wherein the step of recovering from the solid crystals of diacid substituted aromatics a diacid substituted aromatic having a purity of at least 97% comprises a step of contacting the isolated crystals of diacid substituted aromatic with a first solvent for a time period of between about 5 and about 120 minutes at a temperature of between about 140° C. and 200° C.

21. The method of claim 20 wherein the step of recovering from the solid crystals of diacid substituted aromatics a diacid substituted aromatic having a purity of at least 97% comprises a step of contacting separating crystals of diacid substituted aromatics from the first solvent and then contacting the separated crystals of diacid substituted aromatic with a second solvent for a time period of between about 5 and about 120 minutes at a temperature of between about 140° C. and 200° C.

22. The method of claim 21 wherein the first solvent and the second solvent comprise acetic acid.

23. The method of claim 21 wherein the first solvent and the second solvent comprise water.

24. The method of claim 21 wherein the first solvent is acetic acid and the second solvent is water.

25. A method to produce an acid substituted aromatic from an alkyl substituted aromatic, the method comprising the steps of:

providing a feed stream comprising a dialkyl substituted aromatic and in an organic acid solvent:

contacting the feed stream with an oxidant, the oxidant containing at least 50% by volume oxygen and at an oxygen partial pressure of at least 1 psia, at a temperature between about 80° C. and about 130° C., in the presence of a catalyst system comprising zirconium and cobalt, wherein the contacting is done in a stirred tank reactor:

removing from the stirred tank reactor a vapor stream comprising the organic acid, water vapor and unreacted oxidant;

condensing at least a portion of the organic acid and water from the vapor stream;

separating at least a portion of the water from the organic acid back to the stirred tank reactor;

returning at least a portion of the condensed organic acid back to the stirred tank reactor;

continuously recovering from the stirred tank reactor a product comprising a diacid substituted aromatic;

isolating solid crystals of diacid substituted aromatic from the reactor product; and recovering from the solid crystals a diacid substituted aromatic having a purity of at least 97% by weight wherein the isolated solid crystals of diacid substituted aromatics are further contacted with additional solvent and additional oxygen at a temperature between about 120° C. and about 220° C. for a period of between about 5 and about 120 minutes.

26. A method to produce an acid substituted aromatic from an alkyl substituted aromatic, the method comprising the steps of:

providing a feed stream comprising a dialkyl substituted aromatic and in an organic acid solvent:

contacting the feed stream with an oxidant, the oxidant containing at least 50% by volume oxygen and at an oxygen partial pressure of at least 1 psia, at a temperature between about 80° C. and about 130° C., in the presence of a catalyst system comprising zirconium and cobalt, wherein the contacting is done in a stirred tank reactor:

removing from the stirred tank reactor a vapor stream comprising the organic acid, water vapor and unreacted oxidant;

condensing at least a portion of the organic acid and water from the vapor stream;

separating at least a portion of the water from the organic acid back to the stirred tank reactor;

returning at least a portion of the condensed organic acid back to the stirred tank reactor;

continuously recovering from the stirred tank reactor a product comprising a diacid substituted aromatic;

isolating solid crystals of diacid substituted aromatic from the reactor product; and recovering from the solid crystals a diacid substituted aromatic having a purity of at least 97% by weight wherein the isolated crystals of diacid substituted aromatics are further contacted with fresh solvent and additional oxygen at a temperature of between about 150° C. and 200° C. for a period of time between about 10 and about 60 minutes.

27. A method to produce an acid substituted aromatic from an alkyl substituted aromatic, the method comprising the steps of:

providing a feed stream comprising a dialkyl substituted aromatic and in an organic acid solvent:

contacting the feed stream with an oxidant, the oxidant containing at least 50% by volume oxygen and at an oxygen partial pressure of at least 1 psia, at a temperature between about 80° C. and about 130° C., in the presence of a catalyst system comprising zirconium and cobalt, wherein the contacting is done in a stirred tank reactor;

removing from the stirred tank reactor a vapor stream comprising the organic acid, water vapor and unreacted oxidant;

condensing at least a portion of the organic acid and water from the vapor stream;

separating at least a portion of the water from the organic acid back to the stirred tank reactor;

returning at least a portion of the condensed organic acid back to the stirred tank reactor;

continuously recovering from the stirred tank reactor a product comprising a diacid substituted aromatic;

isolating solid crystals of diacid substituted aromatic from the reactor product; and recovering from the solid crystals a diacid substituted aromatic having a purity of at least 97% by weight wherein the removed vapor stream is contacted with the reactor feed in a pre-reactor at a temperature of between about 80° C. and about 130° C. for between about 10 and about 30 minutes.

* * * * *